US00PP33444P2

(12) United States Plant Patent
Zaiger et al.

(10) Patent No.: US PP33,444 P2
(45) Date of Patent: Sep. 7, 2021

(54) **INTERSPECIFIC *PRUNUS* TREE NAMED 'SANGRIA RED-2'**

(50) Latin Name: **Interspecific *Prunus* species**
Varietal Denomination: Sangria Red-2

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 16/873,978

(22) Filed: Sep. 4, 2020

(51) Int. Cl.
*A01H 5/08* (2018.01)
*A01H 6/74* (2018.01)

(52) U.S. Cl.
USPC ..... Plt./180

(58) Field of Classification Search
USPC ..... Plt./180, 184, 185, 186
CPC ... A01H 5/08; A01H 5/00; A01H 6/74; A01H 6/7427; A01H 6/7472; A01H 6/7436; A01H 6/7463
See application file for complete search history.

(56) References Cited

U.S. PATENT DOCUMENTS

PP32,878 P2 * 3/2021 Zaiger ..... A01H 6/7427 Plt./180

OTHER PUBLICATIONS

Trademark Electronic Search System (TESS), retrieved on Jun. 15, 2021, retrieved from the Internet at https://tmsearch.uspto.gov/bin/showfield?f=doc&state=4801:oy08yz.2.6, 2 pp. (Year: 2021).*

* cited by examiner

*Primary Examiner* — June Hwu

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree having a vigorous, upright growth habit.
2. Tree being a regular and productive bearer of medium size, red flesh fruit.
3. Fruit with a high degree of attractive reddish-purple skin color.
4. Fruit with good flavor and eating quality.
5. Fruit with good storage and shipping ability.

1 Drawing Sheet

Botanical designation: Interspecific *Prunus* species.
Variety denomination: 'Sangria Red-2'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecific and apricot trees, which are known to us, and mentioned herein, 'Bella Jewel' Interspecific (U.S. Plant Pat. No. 23,106), 'Bella Cerise' Interspecific (U.S. Plant Pat. No. 18,815), 'Flavorosa' Interspecific (U.S. Plant Pat. No. 10,285), and the proprietary non-patented interspecific seedling selections '76MA153', '19ZD725' and the proprietary non-patented apricot '160LH337'.

STATEMENT REGARDING FEDERALLY SPONSORED RESEARCH AND DEVELOPMENT

Not applicable.

ORIGIN OF THE VARIETY

The new and distinct variety of interspecific tree was developed by us in our experimental orchard located near Modesto, Calif. from a first generation cross between 'Bella Jewel' Interspecific (U.S. Plant Pat. No. 23,106) and our proprietary non-patented interspecific seedling selection '76MA153'. The pollen parent (76MA153) originated as an open pollinated seedling selection from the proprietary non-patented interspecific seedling '19ZD725', which originated from a first generation cross between our proprietary apricot seedling '160LH337' and 'Bella Cerise' Interspecific (U.S. Plant Pat. No. 18,815). A large number of these first generation seedlings were grown and budded onto older trees of 'Nemaguard' Rootstock (non-patented) to accelerate rapid fruit production. Under close and careful observation we recognized the desirable tree and fruit characteristics of the present seedling and selected it in 2014 for additional asexual propagation and commercialization.

ASEXUAL REPRODUCTION OF THE VARIETY

In 2014 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new and distinct variety of interspecific tree is of large size, vigorous, upright growth and a regular and productive bearer of medium size, clingstone fruit with an attractive reddish purple skin color. The fruit is further characterized by its firm, red flesh, good flavor and eating quality with good handling and shipping ability. In comparison to its seed parent 'Bella Jewel' Interspecific (U.S. Plant Pat. No. 23,106) the fruit of the new variety is approximately 21 days later in maturity. In comparison to its proprietary non-patented interspecific pollen parent '76MA153' the fruit of the new variety is approximately 48 days later in maturity. In comparison to the commercial variety 'Flavorosa' Interspecific (U.S. Plant Pat. No. 10,285) the fruit of the new variety is approximately 4 days later in maturity and has an attractive reddish purple skin color compared to dark red.

DESCRIPTION OF THE PHOTOGRAPH

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 6 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 6 year old specimens grown near Modesto, Calif., with color in accordance with Munsell Book of Color published in 1958.

Tree:

*Size*.—Large, pruned to 3 to 3.5 meters in height and width for economical harvesting of fruit. Varies with different cultural practices.

*Vigor*.—Vigorous, tree growth of 1.5 to 2 meters the first growing season. Varies with cultural practices, soil type, fertility and climatic conditions.

*Form*.—Upright growth, usually pruned to vase shape.

*Branching habit*.—Upright, crotch angle approximately 30°, increases with heavy crop load.

*Productivity*.—Productive, thinning and spacing of fruit necessary for desired market size fruit. Number of fruit set varies with climatic conditions during blooming period.

*Bearer*.—Regular, has had adequate fruit set 4 consecutive years. No alternate bearing observed.

*Fertility*.—Self sterile, pollinator required.

*Density*.—Medium dense, usually pruned to vase shape to increase air movement and sunlight to enhance fruit color and health of fruit spurs.

*Hardiness*.—Hardy in all stone fruit growing areas of California. Tree grown in USDA Hardiness Zone 9. Winter chilling requirement approximately 650 hours at or below 45° F.

Trunk:

*Size*.—Medium, average circumference 58.4 cm at 25.4 cm above ground on a 6 year old tree.

*Stocky*.—Medium stocky.

*Texture*.—Medium shaggy, roughness increases with age of tree.

*Color*.—Varies from 10YR 4/2 to 10YR 2/2.

Branches:

*Size*.—Medium. Average circumference 11.2 cm at 1.2 meters above ground. Crotch angle approximately 30°, increases with heavy crop load.

*Surface texture*.—New growth relatively smooth. Mature growth medium rough, roughness increases with age.

*Lenticels*.—Average number 44 in a 25.8 square cm area. Average length 5.0 mm. Average width 1.5 mm. Color 10YR varies from 6/10 to 10YR 5/10.

*Color*.—New growth varies from 5GY 7/8 to 5GY 5/8. Mature growth varies from 7.5YR 3/4 to 7.5YR 2/4, varies with age of growth.

Leaves:

*Size*.—Medium. Average length 93.7 mm. Average width 39.6 mm.

*Form*.—Elliptical.

*Apex*.—Acuminate.

*Base*.—Cuneate.

*Margin*.—Serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 19.5 mm. Average width 1.8 mm. Longitudinally grooved. Surface — glabrous. Color varies from 5GY 6/4 to 5GY 6/6.

*Glands*.—Type — reniform. Size — small. Average length 1.0 mm. Average diameter 0.1 mm. Average number 3, varies from 1 to 4. Located primarily on the base of the leaf blade and upper portion of the petiole. Color 5GY 5/6.

*Stipules*.—None present at time of measurement.

*Color*.—Upper surface varies from 7.5GY 3/4 to 7.5GY 2/4. Lower surface varies from 5GY 6/4 to 5GY 5/4. Midvein color varies from 5GY 8/4 to 5GY 7/4.

Flower buds:

*Size*.—Medium. Average length 10.3 mm. Average diameter 6.5 mm.

*Hardiness*.—Hardy with respect to California winters.

*Density*.—Dense.

*Form*.—Conical, becoming elongated just before opening.

*Pedicel*.—Average length 6.8 mm. Average width 0.8 mm. Surface — glabrous. Color varies from 2.5GY 7/6 to 2.5GY 7/8.

*Color*.—N 9.5/(white).

*Number of buds per spur*.—Average number 6, varies from 4 to 8. Varies with age of spur.

Flowers:

*Blooming period*.—Date of First Bloom Feb. 25, 2020. Date of Petal Fall Mar. 6, 2020, varies slightly with climatic conditions.

*Size*.—Medium. Average height 11.1 mm. Average diameter 21.5 mm.

*Petals*.—Number — normally 5, alternately arranged to sepals. Size — medium. Average length 11.7 mm. Average width 8.2 mm. Petal apex — rounded. Petal base — truncate. Form — elliptical. Arrangement — free. Margin — sinuate. Color N 9.5/(white). Both upper and lower surfaces — glabrous.

*Sepals*.—Number — normally 5, alternately arranged to petals. Size — small to medium. Average length 3.4 mm. Average width 3.0 mm. Shape — ovate to triangular. Apex — ovate. Margin — entire. Both upper and lower surfaces glabrous. Color — upper surface varies from 5GY 6/6 to 5GY 5/8. Lower surface varies from 5GY 6/6 to 5GY 5/6.

*Stamens*.—Average number per flower 33, varies from 30 to 35. Average filament length 7.6 mm. Filament color N 9.5/(white). Anther color varies from 5Y 8/8 to 5Y 7/8.

*Pollen*.—Self sterile, pollinator required. Color varies from 2.5Y 7/12 to 5Y 7/12.

*Pistil*.—Number — normally one. Average length 10.0 mm. Position of stigma even with anthers. Surface — glabrous. Color varies from 10Y 8/4 to 2.5GY 8/4.

*Fragrance*.—Moderate aroma.

*Color*.—N 9.5/(white).

*Pedicel*.—Average length 11.2 mm. Average width 1.3 mm. Surface — glabrous. Color varies from 2.5GY 7/8 to 2.5GY 6/6.

*Number flowers per flower bud*.—Average number 2, varies from 2 to 3.

Fruit:

*Maturity when described*.—Firm ripe and ready for consumption.

*Date of first picking*.—May 28, 2020.

*Date of last picking*.—Jun. 7, 2020, varies slightly with climatic conditions.

*Size*.—Medium. Average diameter axially 49.2 mm. Average transversely in suture plane 59.6 mm. Average weight 110.7 grams, varies slightly with fertility of the soil, amount of thinning and climatic conditions.

*Form*.—Globose.

*Suture*.—Slightly lipped, some fruit with slight suture.

*Ventral surface*.—Slightly lipped.

*Apex*.—Nearly rounded.

*Base*.—Retuse.

*Stem cavity*.—Rounded to slightly elongated in suture plane. Average depth 7.6 mm. Average diameter 7.3 mm.

Stem:

*Size*.—Small. Average length 12.9 mm. Average diameter 2.0 mm.

*Color*.—Varies from 10Y 5/6 to 2.5GY 5/8.

Flesh:

*Ripens*.—Slightly early at apex.

*Texture*.—Firm, meaty.

*Fibers*.—Few, small, tender.

*Firmness*.—Firm, comparable to other commercial interspecific varieties.

*Aroma*.—Slight.

*Amydgalin*.—Undetected.

*Eating quality*.—Good.

*Flavor*.—Good.

*Juice*.—Moderate amount, enhances flavor.

*Acidity*.—Not available.

*Brix*.—Average Brix 13.0°, varies slightly with amount of fruit per tree and climatic conditions.

*Color*.—Varies from 7.5R 3/10 to 5R 4/10.

*Pit cavity*.—Average length 24.0 mm. Average width 23.5 mm. Average depth 8.0 mm. Color varies from 5R 3/4 to 7.5R 2/6.

Skin:

*Thickness*.—Medium.

*Surface*.—Smooth.

*Bloom*.—Moderate amount, complete coverage.

*Tendency to crack*.—None.

*Color*.—Ground color varies from 10Y 5/6 to 2.5GY 6/4. Overspread with 5R 3/8 to 7.5R 2/8. Very small, randomly spaced areas of ground color exposed to give a speckling pattern to surface areas.

*Tenacity*.—Tenacious to the flesh.

*Astringency*.—Slight to none.

Stone:

*Type*.—Clingstone, strong adherence to flesh.

*Size*.—Medium. Average length 23.0 mm. Average width 22.5 mm. Average thickness 14.0 mm.

*Form*.—Obovoid.

*Base*.—Flat.

*Apex*.—Pointed. Average length 1.2 mm.

*Surface*.—Pitted throughout, pits vary from round to elongated.

*Sides*.—Unequal, one side extending slightly further from the suture plane.

*Ridges*.—A small ridge on each side of suture extending from base to apex.

*Tendency to split*.—None.

*Color*.—Varies from 7.5YR 5/8 to 10YR 6/8, when dry.

Kernel:

*Size*.—Medium. Average length 13.8 mm. Average width 12.5 mm. Average depth 7.9 mm.

*Form*.—Ovate.

*Viability*.—Viable, complete embryo development.

*Skin color*.—Varies from 5Y 9/4 to 7.5Y 9/4.

Use:

*Dessert*.—Market — local and long distance.

Keeping quality: Good, held firm in cold storage 3 weeks at 38° to 42° F. without shriveling, internal breakdown of flesh or appreciable loss of flavor.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices. The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific *Prunus* tree named 'Sangria Red-2', substantially as illustrated and described.

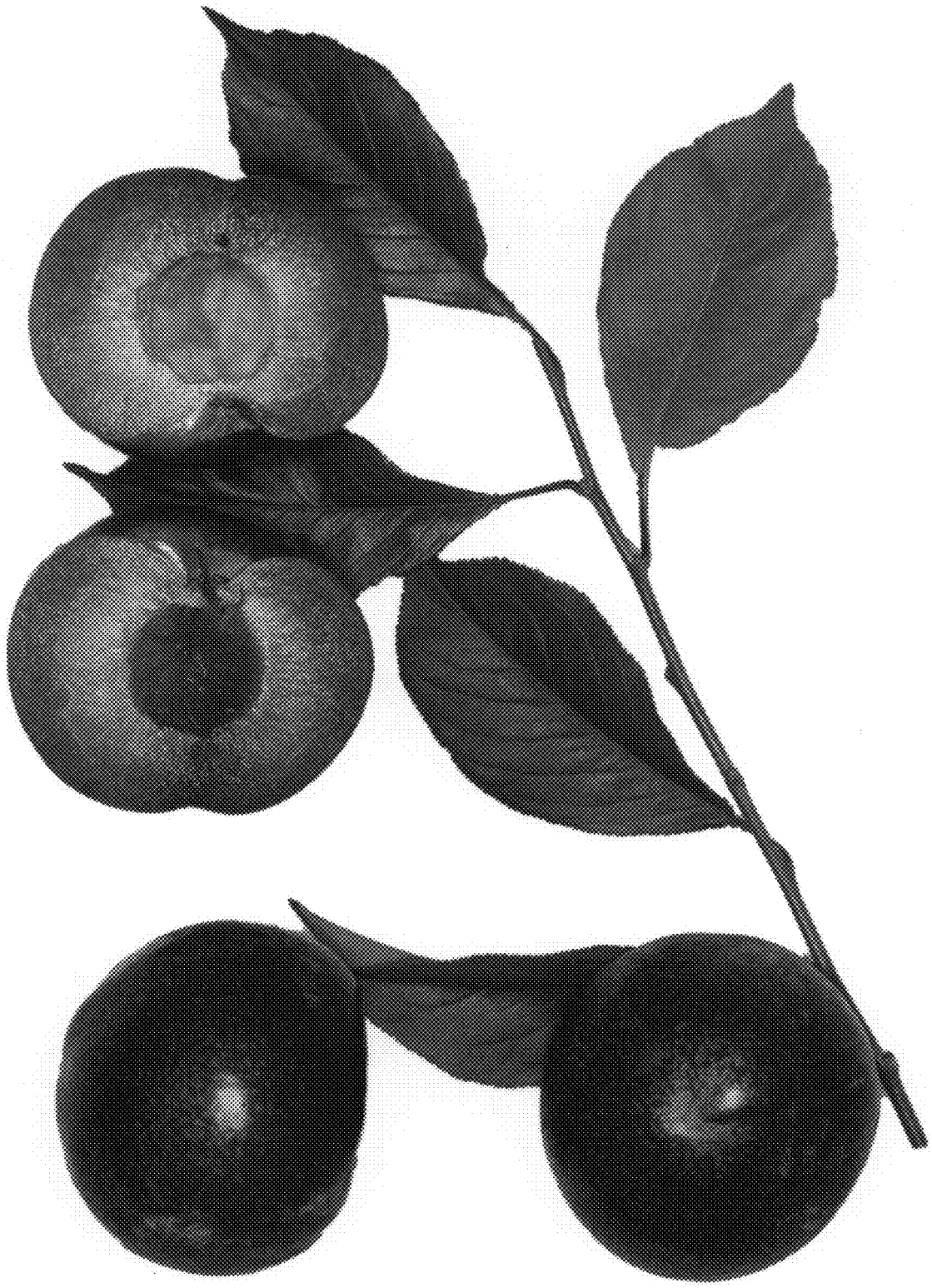

* * * * *